United States Patent [19] [11] 4,404,284
Heider et al. [45] Sep. 13, 1983

[54] MEASUREMENT OF VOLATILE CONSTITUENTS OF A CULTURE MEDIUM

[75] Inventors: Manfred Heider, Brunn; Josef Hofschneider, Gramatneusiedl; Wolfgang Schallenberger, Graz; Franz Nodes, Vienna; Eberhard Kempe, Hetzmannsdorf, all of Austria

[73] Assignee: Vogelbusch Gesellschaft m.b.H., Vienna, Austria

[21] Appl. No.: 331,226

[22] Filed: Dec. 16, 1981

[30] Foreign Application Priority Data

Dec. 17, 1980 [AT] Austria .................................. 6153/80

[51] Int. Cl.$^3$ ............................................. C12M 1/34
[52] U.S. Cl. .................................... 435/291; 435/817; 73/19
[58] Field of Search ................... 73/19; 422/90, 98; 435/241, 817; 137/590, 592

[56] References Cited

U.S. PATENT DOCUMENTS 3,084,472  4/1963  Feik ............................. 137/592 X
3,661,010  5/1972  Neuwelt ........................ 73/19 X
4,315,990  2/1982  Sheets .......................... 435/291

FOREIGN PATENT DOCUMENTS 2310164  9/1973  Fed. Rep. of Germany .
457912  8/1968  Switzerland .

Primary Examiner—Ferris H. Lander
Attorney, Agent, or Firm—Toren, McGeady and Stanger

[57] ABSTRACT

A device for measuring volatile constituents of a culture medium in the fermentation industry, comprising a probe, which has a permeable membrane to exchange material for a carrier medium, and a sensor responding to the content of the substance to be measured which has permeated into the carrier medium. In order that the device may be used in industrial fermenters and in order to achieve a high degree of accuracy in measurement and reproducibility of the measured values, both the permeable membrane and the sensor are disposed in the space in which the culture medium to be tested is situated, the probe being introduced into the space containing the culture medium where appropriate by way of a lock.

3 Claims, 1 Drawing Figure

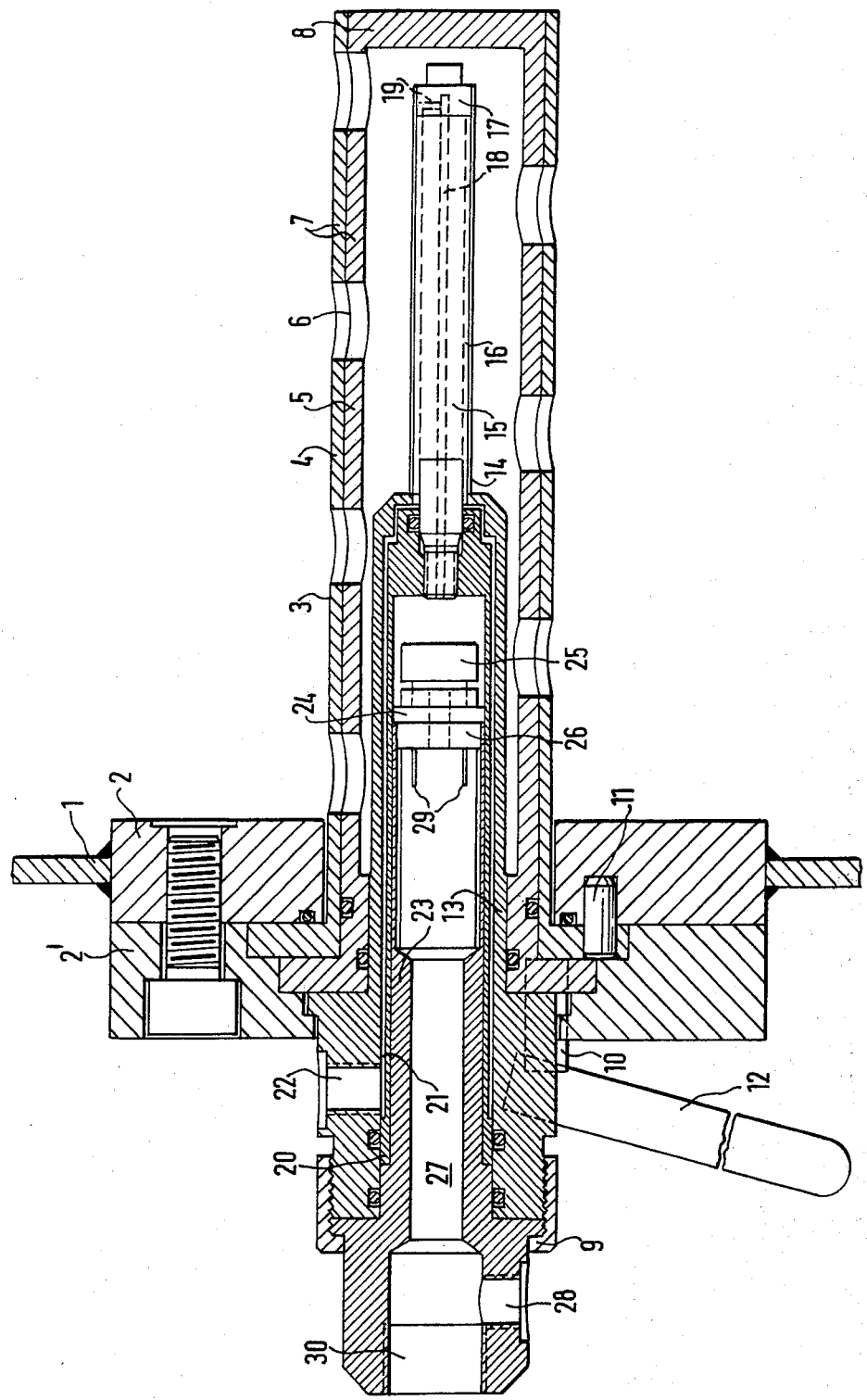

MEASUREMENT OF VOLATILE CONSTITUENTS OF A CULTURE MEDIUM

The present invention relates to the measurement of volatile constituents of a culture medium in the fermentation industry, in particular a device comprising a probe, which has a permeable membrane to exchange material for a carrier medium, and a sensor responding to the content of the substance to be measured which has permeated into the carrier medium.

In the case of a known device of this type, the carrier medium is fed from the permeable membrane immersed in the culture medium, by way of a capillary duct, to the sensor, which is disposed in an analysing apparatus situated outside the fermentation container. Such a design has the disadvantage that as it travels from the probe to the sensor the carrier medium is subjected to temperature fluctuations, as a result of which measurement errors arise. As a rule, cooling takes place, since the temperature of the culture medium is higher than the temperature of the room in which the fermenter containing the culture medium is situated. If a gaseous carrier medium is used, cooling will lead to condensation of high-boiling constituents of the gas to be analysed, so that the measured values are not reproducible. In addition, the measurement values may be distorted by external influences, such as draught or the sun's radiation.

It is an object of the present invention to overcome these disadvantages.

The present invention provides a device for measuring volatile constituents of a culture medium, comprising a probe, which has a permeable membrane to exchange material for a carrier medium, and a sensor responding to the content of the substance to be measured which has permeated into the carrier medium, wherein both the permeable membrane and the sensor are disposed in the space in which the culture medium to be tested is situated, the probe being introduced into the space containing the culture medium where appropriate by way of a lock.

In the device of the invention, after passing through the permeable membrane, the carrier medium enriched with volatile constituents which have permeated through reaches the sensor, without being subjected to a temperature fluctuation, so as to permit a precise, reproducible measurement which reflects the actual conditions in an undistorted manner, it also being possible where necessary to replace the probe when the fermenter is filled.

In a probe for the device according to the invention a silicone tube known per se may advantageously be arranged as a permeable membrane around a solid core, the outer wall of which has one or more ducts preferably extending helically, the ducts being connected to a supply line and an outlet line for the carrier medium and the outlet line leading to the sensor which is directly disposed in a probe member projecting into the space containing the culture medium. Such a design has the advantage that the probe may also be used in fermenters of industrial size, in which the permeable membrane is subjected to considerable stresses and pressures. In addition, by virtue of the helical course of the duct or ducts a fast rate of travel of the gas in the carrier gas space may be attained with a very small quantity of carrier gas. In this way a high concentration gradient is achieved, namely because the carrier gas has a relatively long path of contact with the membrane.

Furthermore, the core may be in the form of a rod which is provided with an external thread forming the duct or ducts and with a blind-end bore which extends in the axial direction almost through the whole of the rod and which is connected to the courses of the external thread by a further bore provided in the region of the closed end of the blind-end bore, thereby achieving a particularly simple construction of the core of the probe. Advantageously, the rod forming the core may be secured, at its end provided with the outlet of the blind-end bore, to the probe member, and the supply line for the carrier medium at this end may open from the outside into the interspace between the wall of the thread and the silicone tube, so that the carrier medium is fed to the sensor by means of the probe member and led out of the probe. In this connection the sensor may be disposed directly opposite the outlet of the blind-end bore through which the carrier medium enriched with the substance to be measured is led out of the probe member, whereby the carrier medium enriched with the volatile constituents reaches the sensor immediately after passing through the permeable membrane, so that no reactions can take place between the carrier medium and the volatile constituents before the latter have been measured by the sensor.

A lock for the device according to the invention may comprise perforated tubes which are slid one into the other in a sealing manner and the inner one of which is closed off at its end projecting into the container containing the culture medium to be tested, the two tubes being rotatable relative to one another between two end positions and the holes of the tubes being superimposed in one end position and the holes of each tube facing a solid wall portion of the respective other tube in the other end position, so that in addition a mechanical protection is provided for the probe.

The invention will be further described, by way of example only, with reference to the accompanying drawing, which is a longitudinal section of one embodiment of the invention.

The drawing shows a wall 1 of a fermentation container in which a flange is provided which consists of two parts 2 and 2' which may be screwed together. A lock 3, which comprises two perforated tubes 4 and 5 slid one into the other in a sealing manner and projecting into the interior of the container, is secured to the wall 1 in a sealing manner by means of the flange. The two tubes may be rotated relative to one another in such a way that in one end position the holes 6 of the tubes are superimposed and in the other end position each hole 6 of one tube faces a solid wall portion 7 of the other tube. The end of the inner tube 5 towards the interior of the container is closed by a plate 8, so that after the inner tube 5 has been rotated into its other end position the interior of the tube 5 is closed off from the interior of the container. In this mutual rotational position of the tubes 4 and 5 of the lock 3, a probe 9 is inserted into the lock 3 and is secured in the part 2' of the flange by means of a bayonet socket. A pin 10, which engages in a corresponding bore in the inner tube 5, is disposed on the probe 9, so that as the probe is rotated in order to close the bayonet socket the inner tube 5 is co-rotated with the probe 9. The outer tube 4 is prevented from rotating by a pin 11 engaging in a bore in the part 2 of the flange. The probe 9 is provided with a handle 12 in order that it may be rotated.

The probe 9 is provided with a probe support 13 on which the pin 10 and the bayonet socket are disposed. At the end of the probe support 13 projecting into the interior of the container a permeable membrane 14 is provided which is formed by a silicone hose or tube and which is slid on to a cylindrical core 15 which is secured to the probe support 13 and the outer wall of which is provided with a thread whose courses are closed off by the silicone tube forming the permeable membrane 14. In this way one or more helically extending ducts 16, through which carrier medium flows during operation, are formed, according to the pitch of the thread, between the outer wall of the core 15 and the permeable membrane. An area 17 without thread is left at the free end of the core 15 in order to close off the ducts 16 from the contents of the container. The core 15 is provided with a blind-end bore 18 which extends in its longitudinal direction and passes through almost the whole of the core and only terminates in the area 17 without thread. In this area a bore 19 is provided, through which the blind-end bore 18 is connected to the ducts 16 formed by the courses of the thread. The probe support 13 is made hollow, a tubular member 20 being inserted in the respective cavity, while leaving an interspace between the walls so as to form a duct 21 which is connected to the end of the ducts 16 towards the probe support and which is provided with a connecting socket 22 leading outwards for the carrier medium supply.

A sensor support 23 is inserted coaxially into the tubular member 20 and its end towards the core 15 is provided with a base 24 for a sensor 25 in such a way that the latter is arranged directly opposite the outlet of the blind-end bore 18 conveying the carrier medium out of the core 15. The carrier medium passing through the sensor 25 and enriched with volatile components flows out of the probe 9 through a bore 26 in the base 24, a bore 27 passing through the sensor support 23 in the axial direction and a lateral outlet socket 28. Electrical terminals 29 are provided on the base 24. Measurement leads (not shown) are led through the bore 27 and out of the probe 9, the bore being closed at its end projecting out of the container by means of a plug 30 which may be provided with ducts for the measurement leads. The probe may be connected by these measurement leads to a microprocessor which then controls for example the supply of nutrient solution as a function of the measurement values arriving from the sensor.

When the probe 9 is inserted into the lock 3 the two tubes 4 and 5 of the lock are arranged in the mutual rotational position in which the holes 6 of the tubes 4,5 are closed by the wall portions 7 of the other tube in each case. When the probe 9 is fully inserted, the pin 10 of the probe engages in the corresponding bore in the inner tube 5. If the probe 9 is now locked when turning by means of the bayonet socket, the inner tube 5 will be simultaneously rotated into its end position in which the holes 6 of the tubes 4,5 lie opposite one another, so that culture medium may flow through the interior of the lock and, in this way, the permeable membrane 14 comes into contact with the culture medium. A carrier medium, in this case compressed air, is fed through the connecting lock 22 and the duct 21 into the ducts 16 formed by the thread, where the volatile constituents to be measured permeate through the membrane 14 into the carrier medium from the culture medium. The carrier medium then passes through the bore 19 at the front end of the core 15 supporting the permeable membrane 14 into the blind-hole bore 18 extending in the axial direction of the core 15 and immediately after leaving the bore 18 flows directly to the sensor 25, flows through the latter and leaves the probe 9 by way of the bore 26 in the base 24 of the sensor, the bore 27 in the sensor support 23 and the outlet socket 28. The sensor 25 reacts to the proportion of volatile substances by a change in the line resistance and thus delivers a measurement signal for the microprocessor which then performs the necessary control steps as a function of this measurement signal.

If the probe 9 has to be removed from the lock 3, for example for cleaning, it is turned by the handle 12 in order to release the bayonet socket and thus the inner tube 5 of the lock 3 is simultaneously turned to such an extent by the pin 10 that the holes 6 of the tubes 4,5 are covered by the solid wall portions 7 of the other tube in each case, and the lock 3 is thereby closed.

We claim:

1. A probe for measuring volatile constituents of a culture medium in the fermentation industry comprising an axially elongated pin having a first end and a second end and having an outer surface extending in the first end - second end direction, at least one helical groove formed in said outer surface and extending in the first end - second end direction, a permeable membrane fitted over the outer surface of said pin and forming a closure over said at least one helical groove so that said helical groove forms a closed flow path, said pin is arranged to extend into a fermentation container and said permeable membrane is arranged to pass volatile constituents from the fermentation container into a carrier medium flowing through said at least one helical groove, said pin forming a blind end bore open at the second end and closed at the first end of said pin, said pin having at least one transverse bore adjacent the first end thereof and interconnecting said blind bore and said at least one helical groove, a probe member, a sensor located within said probe member for responding to the volatile constituents within the carrier medium, said probe member arranged to extend into the fermentation container, said pin supported by and extending from said probe member with the second end of said pin located within said probe member and with the open end of said blind bore opening into said probe member.

2. A probe, as set forth in claim 1, wherein said probe member forming an open space therein, said blind bore opening into said open space, and said sensor located within said open space opposite the opening from said blind bore, and said open space within said probe member and containing said sensor is arranged to extend into the fermentation container.

3. A probe, as set forth in claim 1, including means for supplying the carrier medium into said probe member and into the end of said at least one helical groove adjacent the second end of said pin, said means including a carrier medium inlet extending through the wall of said probe member arranged to be located outwardly from the fermentation container when said probe is inserted into said fermentation container.

* * * * *